US006605602B1

(12) United States Patent
Vats

(10) Patent No.: US 6,605,602 B1
(45) Date of Patent: Aug. 12, 2003

(54) METHOD OF TREATING BK VIRUS NEPHROPATHY

(75) Inventor: Abhay N. Vats, Wexford, PA (US)

(73) Assignee: University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 10/238,483

(22) Filed: Sep. 10, 2002

Related U.S. Application Data

(62) Division of application No. 09/967,025, filed on Sep. 28, 2001.

(51) Int. Cl.[7] ............................................. A61K 31/675
(52) U.S. Cl. ............................ 514/85; 514/86; 514/256
(58) Field of Search ................................. 514/258–260, 514/256–269, 86, 85

(56) References Cited

PUBLICATIONS

*Applied Biosystems*, User Bulletin #5, "Multiplex PCR with TaqMan VIC Probes," pp. 1–20, Aug. 10, 1998 (updated Jan. 2001).

Arthur, Ray R., et al. "Detection of BK Virus and JC Virus in Urine and Brain Tissue by the Polymerase Chain Reaction," *Journal of Clinical Microbiology*, vol. 27, No. 6, pp. 1174–1179 (Jun. 1989).

Baksh, Fabien K., et al. "Molecular Genotyping of BK and JC Viruses in Human Polyomavirus–Associated Interstital Nephritis After Renal Transplantation," *American Journal of Kidney Diseases*, vol. 38, No. 2, pp. 354–365 (Aug. 2001).

Biel, Stean S., et al., "Rapid Quantification and Differentiation of Human Polyomavirus DNA in Undiluted Urine from Patients after Bone Marrow Transplantation," *Journal of Clinical Microbiology*, vol. 38, No. 10, pp. 3689–3695 (Oct. 2000).

Boldorini, Renzo, et al., "Cytologic and Biomolecular Diagnosis of Polyomavirus Infection in Urine Specimens of HIV–Positive Patients," *Acta Cytologica*, vol. 44, No. 2, pp. 205–210 (Mar.–Apr. 2000).

Boldorini, Renzo, et al., "Molecular Characterization and Sequence Analysis of Polyomavirus BKV–Strain in a Renal–Allograft Recipient," *Human Pathology*, vol. 32, No. 6, pp. 656–659 (Jun. 2001).

Jin, Li, "Molecular Methods for Identification and Genotyping of BK Virus," *Methods in Molecular Biology*, vol. 165, pp. 33–48 (2001).

Jin, Li and Gibson, P.E., "Genomic Function and Variation of Human Polyomavirus BK (BKV)," *Reviews in Medical Virology*, vol. 165, pp. 201–214 (1996).

Jin, Li, et al., "Genomic Typing of BK Virus in Clinical Specimens by Direct Sequencing of Polymerase Chain Reaction Products," *Journal of Medical Virology*, vol. 41, pp. 11–17 (1993).

Jin, Li, "Rapid Genomic Typing of BK Virus Directly from Clinical Specimens," *Molecular and Cellular Probes*, vol. 7, pp. 331–334 (1993).

Limaye, Ajit P., et al., "Quantitation of BK Virus Load in Serum for the Diagnosis of BK Virus–Associated Nephropathy in Renal Transplant Recipients," *The Journal of Infectious Diseases*, vol. 183, pp. 1669–1672 (2001).

Nickeleit, Volker, et al., "BK–Virus Nephropathy in Renal Transplants—Tubular necrosis, MHC–Class II Expression and Rejection in a Puzzling Game," *Nephrol Dial Transplant*, vol. 15, pp. 324–332 (2000).

Pappo, O., et al., "Human Polyoma Virus Infection of Renal Allografts: Histopathologic Diagnosis, Clinical Significance, and Literature Review," *Modem Pathology*, vol. 9, No. 2, pp. 105–109 (1996).

Seif, Isabelle, et al., "The Genome of Human Papovavirus BKV," *Cell*, vol. 18, pp. 963–977 (Dec. 1979).

Vats, Abhay N., et al., "Development of Quantitative PCR for BK Virus Detection in Urine and its Role in Management of Allograft Viral Infection Masquerading as Acute Rejection" *American Society of Transplantation*, Chicago, IL, May 2000.

BK virus strain Dunlop, complete genome. GenBank Accession No.: J02038.

BK virus, complete genome, GenBank Accession No.: NC 001538.

Nickeleit et al (New England Journal of Medicine 342: 1309–1315, May 4, 2000).*

Randhawa et al (New England Journal of Medicine 342:1361–1363, May 4, 2000).*

Held et al (Bone Marrow Transplantation 26(3): 347–350, Aug. 2000).*

Gonzales–Fraile et al (Transplant Infectious Disease 3(1): 44–46, Mar. 2001).*

Andrei et al (Antimicrobial Agents and Chemotherapy 41(3): 587–593, Mar. 1997).*

* cited by examiner

*Primary Examiner*—Mary E. Mosher
(74) *Attorney, Agent, or Firm*—Kirkpatrick & Lockhart LLP

(57) ABSTRACT

Provided are oligonucleotides for the quantitation of BK virus (BKV) viral loads in a sample and methods for the diagnosis and management of BKV-associated nephropathy using PCR or QPCR methods. In addition, a PCR method for quantitating the BKV viral load in urine, serum and tissue using the described nucleic acid primers is also disclosed. Furthermore, a method for the management of BKV-associated nephropathy in renal transplant recipients using cidofovir is disclosed. Lastly, a kit is provided containing the described PCR for use in diagnosing and managing BKV-associated nephropathy.

10 Claims, 2 Drawing Sheets

(SEQ ID NO: 3)

```
   1 ttttgcaaaa attgcaaaag aatagggatt tccccaaata gttttgctag gcctcagaaa
  61 aagcctccac acccttacta cttgagagaa agggtggagg cagaggcggc ctcggcctct
 121 tatatattat aaaaaaaaag gccacaggga ggagctgctt acccatggaa tgcagccaaa
 181 ccatgacctc aggaaggaaa gtgcatgact cacaggggaa tgcagccaaa ccatgacctc
 241 aggaaggaaa gtgcatgact cacagggagg agctgcttac ccatggaatg cagccaaacc
 301 atgacctcag gaaggaaagt gcatgacaga catgttttgc gagcctagga atcttggcct
 361 tgtccccagt taaactggac aaaggccatg gttctgcgcc agctgtcacg acaagcttca
 421 gtgaaagttg gtaaacctg gactggaaca aaaaaaagag ctcagaggat ttttattttt
 481 attttagagc ttttgctgga attttgtaga ggtgaagaca gtgtagacgg gaaaaacaaa
 541 agtaccactg ctttacctgc tgtaaaagac tctgtaaaag actcctaggt aagtaatccc
 601 tttttttttg tatttccagg ttcatgggtg ctgctctagc acttttgggg gacctagttg
 661 ccagtgtatc tgaggctgct gctgccacag gattttcagt ggctgaaatt gctgctgggg
 721 aggctgctgc tgctatagaa gttcaaattg catcccttgc tactgtagag ggcataacaa
 781 gtacctcaga ggctatagct gctataggcc taactcctca aacatatgct gtaattgctg
 841 gtgctcctgg ggctattgct gggtttgctg ctttaattca aactgttagt ggtattagtt
 901 ccttagctca agtagggtat aagttctttg atgattggga tcacaaagtt tccactgtag
 961 gcctctatca gcaatcaggc atggctttgg aattgtttaa cccagatgag tactatgata
1021 ttctgtttcc tggtgtaaat acttttgtta ataatattca ataccttgat cctaggcatt
1081 ggggtccttc tttgtttgct actatttccc aggctttgtg gcatgttatt agggatgata
1141 taccttctat aacctcacag gaattgcaga gaagaacaga agattttttt agagactcct
1201 tggctagatt tttggaggaa actacctgga caattgtaaa tgcccctata aactttata
1261 attatattca acaatattat tctgatcttt ccctattag gccctaatg gttagacaag
1321 tagctgaaag ggaaggtacc cgtgtacatt ttggccatac ttatagtata gatgatgctg
1381 acagtataga agaagttaca caaagaatgg acttaagaaa tcaacaaagt gtacattcag
1441 gagagtttat agaaaaaact attgccccag gaggtgctaa tcaaagaact gctcctcaat
1501 ggatgttgcc tttacttcta ggcctgtacg ggactgtaac acctgctctt gaagcatatg
1561 aagatggccc caaccaaaag aaaaggagag tgtccagggg cagctcccaa aaagccaaag
1621 gaacccgtgc aagtgccaaa actactaata aaaggaggag tagaagttct agaagttaaa
1681 actggggtag atgctattac agagtagaa tgcttcctaa acccagaaat gggggatcca
1741 gatgaaaacc ttagggggctt tagtctaaag ctaagtgctg aaaatgactt tagcagtgat
1801 agcccagaga gaaaaatgct tccctgttac agcacagcaa gaattccccct ccccaattta
1861 aatgaggacc taacctgtgg aaatctactg atgtgggagg ctgtaactgt acaaacagag
1921 gttattggaa taactagcat gcttaacctt catgcagggt cacaaaaagt gcatgagcat
1981 ggtggaggaa aacctattca aggcagtaat ttccacttct ttgctgtagg tggagaaccc
2041 ttggaaatgc agggagtgct aatgaattac aggtcaaagt accctgatgg tactataacc
2101 cctaaaaacc caacagccca gtccaggta atgaatactg accataaggc ctatttggac
2161 aaaaacaatg cttatccagt tgagtgctgg gtacctgatc ccagtagaaa tgaaaatgct
2221 aggtattttg ggactttcac aggaggggaa aatgttcccc cagtacttca tgtgaccaac
2281 acagctacca cagtgttgct agatgaacag ggtgtggggc ctctttgtaa agctgatagc
2341 ctgtatgttt cagctgctga tatttgtggc ctgtttacta acagctctgg aacacaacag
2401 tggagaggcc ttgcaagata ttttaagatc cgcctgagaa aaagatctgt aaagaatcct
2461 tacccaattt ccttttgct aagtgacctt ataaacagga gaacccagag agtggatggg
2521 cagcctatgt atggtatgga atcccaggta gaagaggtta gggtgtttga tggcacagaa
```

FIGURE 1/1

```
2581 agacttccag gggacccaga tatgataaga tatattgaca aacagggaca attgcaaacc
2641 aaaatgcttt aaacaggtgc ttttattgta catatacatt taataaatgc tgcttttgta
2701 taagccactt ttaagcttgt gttattttgg gggtggtgtt ttaggccttt taaaacactg
2761 aaagccttta cacaaatgca actcttgact atggggtct gacctttggg aatcttcagc
2821 aggggctgaa gtatctgaga cttgggaaga gcattgtgat tgggattcag tgcttgatcc
2881 atgtccagag tcttcagttt ctgaatcctc ttctcttgta atatcaagaa tacatttccc
2941 catgcatata ttatatttca tccttgaaaa agtatacata cttatctcag aatccagcct
3001 ttccttccat tcaacaattc tagattgtat atcagttgca aaatcagcta caggcctaaa
3061 ccaaattagc agtagcaaca aggtcattcc actttgtaaa attcttttt caagtaagaa
3121 ctctgagttt tgtaaggatt ttcttaaata tattttgggc ctaaaatcta tttgtcttac
3181 aaatctagct tgcagggttt tagggacagg atactcattc attgtaacca agcctggtgg
3241 aaatatttgg gttcttttgt ttaaatgttt cttttctaaa tttaccttaa cacttccatc
3301 taaataatct ctcaaactgt ctaaattgtt tattccatgt cctgaaggca aatcctttga
3361 ttcagctcct gtccttta catcttcaaa aacaaccatg tactgatcta tagctacacc
3421 tagctcaaag gttagccttt ccatgggtag gtttacattt aaggctttac caccacacaa
3481 atctaataac cctgcagcta gtgttgtttt tccactatca atgggacctt taaataacca
3541 gtatcttctt ttaggtacat tgaaaacaat acagtgcaaa aaatcaaata ttacagaatc
3601 cattttaggt agcaaacagt gcagccaagc aacacctgcc atatattgtt ctagtacagc
3661 atttccatga gctccaaata ttaaatccat tttatctaat atatgattga atctttctgt
3721 tagcatttct tccctggtca tatgaagggt atctactctt tttttagcta aaactgtatc
3781 tactgcttgc tgacaaatac ttttttgatt tttactttct gcaaaaataa tagcatttgc
3841 aaagtgcttt tcatgatact taagtgata aggctggtct ttttctgac acttttaca
3901 ctcctctaca ttgtattgaa attctaaata catacctaat aataaaaaca catcctcaca
3961 ctttgtctct actgcatact cagtaattaa tttccaagac acctgctttg tttcttcagg
4021 ctcttctggg ctaaaatcat gctcctttaa gcccccttga atgctttctt ctatagtatg
4081 gtatggatct ctagttaagg cactatatag taagtattcc ttattaacac ccttacaaat
4141 taaaaaacta aaggtacaca gcttttgaca gaaattatta attgcagaaa ctctatgtct
4201 atgtggagtt aaaaagaata taatattatg cccagcacac atgtgtctac taataaaagt
4261 tacagaatat ttttccataa gttttttata cagaatttga gcttttcttt tagtagtata
4321 cacagcaaag caggcaaggg ttcttattact aaatacagct tgactaagaa actggtgtag
4381 atcagaggga aagtctttag ggtcttctac ctttctttt ttttgggtg gtgttgagtg
4441 ttgagaatct gctgttgctt cttcatcact ggcaaacata tcttcatggc aaaataaatc
4501 ttcatcccat ttttcattaa aggaactcca ccaggactcc cactcttctg ttccataggt
4561 tggcacctat aaaaaaaata attacttagg gcctttaat attttattat ttatctaaat
4621 ataagttagt taccttaaag ctttagatct ctgaagggag tttctccaat tatttggacc
4681 caccattgca gagtttcttc agttaggtct aagccaaacc actgtgtgaa gcagtcaatg
4741 cagtagcaat ctatccaaac caagggctct tttcttaaaa attttctatt taaatgcctt
4801 aatctaagct gacatagcat gcaagggcag tgcacagaag gcttttgga acaaataggc
4861 cattccttgc agtacaggt atctgggcaa agaggaaaat cagcacaaac ctctgagcta
4921 ctccaggttc caaaatcagg ctgatgagct accttacat cctgctccat tttttatac
4981 aaagtattca ttctcttcat tttatcctcg tcgccccctt tgtcagggtg aaattcctta
5041 cacttcctta aataagcttt tctcattaag ggaagatttc cccaggcagc tctttcaagg
5101 cctaaaaggt ccatgagctc catggattct tccctgttaa gaactttatc cat
```

FIGURE 1/2

METHOD OF TREATING BK VIRUS NEPHROPATHY

CROSS REFERRENCE TO RELATED APPLICATIONS

This application is a Divisional of U.S. patent application Ser. No. 09/967,025, filed Sep. 28, 2001.

BACKGROUND OF THE INVENTION

1. Field of the Invention

A PCR method is provided for detecting BK virus, and particularly for managing BK virus-associated nephropathy in renal transplant patients along with related PCR primers and primer sets. A method for reducing BK virus viral load also is provided.

2. Description of the Related Art

BK virus (BKV) is a human polyoma virus that was originally isolated from the urine of immunocompromised patients. Since then, a number of BKV variants (subtypes) have been isolated. BKV causes a subclinical (asymptomatic) infection in the majority of the general population within the first 10 years of life. Subsequent to infection, the virus normally remains latent in the kidney. However, the virus may become reactivated at a later point in time as a result of immunosuppression, for example, following renal transplantation.

BKV contains a double stranded DNA (dsDNA) genome. The complete DNA sequence of BKV is approximately 5,100 base pairs, however this varies with each variant of BKV. For example, the Dunlop strain of BKV contains 5,153 base pairs (see, for example, Self et al. (1979), "The Genome of Human Papovavirus BKV," *Cell* 18:963–77, incorporated herein by reference in its entirety). The BKV genome contains a coding region and a non-coding control region, but is functionally divided into three regions. The coding region can be further divided into the early region and the late region. The early region contains the coding sequence for two non-structural proteins: the T-antigen protein and the t-antigen protein. The late region contains the coding sequence for four structural proteins: VP-1, VP-2, VP-3 and the agno protein. The non-coding control region contains the transcriptional control elements for both early and late gene expression, as well as containing the viral origin of replication.

The role of BKV infection in renal allograft dysfunction has been controversial. Studies have reported a range of clinical outcomes, varying from asymptomatic to significant renal dysfunction. However, recent studies have shown that BKV causes nephropathy in up to 5% of renal allografts. In addition, BKV infection in renal transplant recipients can be associated with significant morbidity. The controversy surrounding the role of BKV in renal dysfunction is due to the difficulty in diagnosing and monitoring BKV infection. One problem is that serological and traditional viral culture techniques are either not specific or not readily available. In addition, these techniques may not be practical in situations where rapid diagnosis is required in order to make timely patient management decisions.

The diagnosis of BKV-associated nephropathy (BKVN) usually is made by allograft biopsy. A positive biopsy shows viral inclusion bodies, often associated with variable mononuclear infiltrates, and tubulitis that may resemble acute rejection. Immunohistochemical techniques are not sensitive enough to detect latent virus in biopsies that lack viral inclusion bodies that are otherwise detectable by standard light microscopy. A complicating factor in the diagnosis of BKVN nephropathy is the fact that BKVN can present in many different ways. BKV infection has presented with features that were variably diagnosed as acute rejection, interstitial nephritis, drug toxicity, ureteric stenosis, and also asymptomatic. Thus a great degree of caution and a high index of suspicion are needed for the proper diagnosis and management of BKVN.

Even after BKVN has been properly diagnosed, clinical management remains a significant challenge. No clinically proven anti-polyomavirus drugs are currently available for the management of BKVN even though in vitro studies have demonstrated that several drugs, including retinoic acid derivatives, DNA gyrase inhibitors, cytosine arabinoside and cidofovir, inhibit polyoma viral DNA replication. Although various therapeutic strategies have been suggested and tried, the results are often variable and dismal. As a result, therapy for BKVN is usually based on renal allograft biopsy findings. The difficulty in clinical management is compounded by the fact that even when biopsies show tubulitis, suggesting the possibility of underlying rejection, there is little or no transient response to corticosteroids in most cases. Another possibility for clinical management is to reduce immunosuppression. Although reducing immunosuppression decreases the viral load, it increases the risk of rejection.

Given the challenges posed by the diagnosis and management of BKVN, the development of non-invasive quantitative techniques to monitor viral load can have a significant impact on the clinical management of these cases. For example, quantitation of the viral load would allow a physician to monitor a patient's response to specific anti-viral therapy. In addition, it would allow a physician to lower a patient's level of immunosuppression sufficiently to permit stimulation of anti-viral immunity without reducing it to a point that would precipitate acute rejection.

Several references discuss PCR assays for the detection of BKV in urine and/or blood. However, those references teach primers that bind to and amplify BKV viral DNA in the early (T and t antigen) region. Other references disclose PCR primers that bind to and amplify sequences located in the late region of the BKV genome, and particularly in the VP-1 region (Li Jin, "Molecular Methods for Identification and Genotyping of BK Virus," *Methods in Molecular Biology*, vol. 165, pp. 33–48 (2001), Li Jin, "Rapid Genomic Typing of BK Virus Directly from Clinical Specimens," *Molecular and Cellular Probes*, vol. 7, pp. 331–334 (1993), Li Jin, "Genomic Typing of BK Virus in Clinical Specimens by Direct Sequencing of Polymerase Chain Reaction Products," *J. Medical Virology*, vol. 41, pp. 11–17 (1993), and Baksh et al., "Molecular Genotyping of BK and JC Viruses in Human Polyomavirus-Associated Interstitial Nephritis After Renal Transplantation," *Amer. J. Kidney Disease*, vol. 38, no. 2, pp. 354–365 (August 2001) each of which are incorporated herein by reference in their entirety). These primers function to generate PCR amplicons that were used to distinguish BKV subtypes by PCR combined with restriction enzyme analysis or sequencing analysis.

Cidofovir (HPMPC, Vistide, (S)-1-(3-hydroxy-2-phosphonylmethoxypropyl) cytosine) is an acyclic nucleoside phosphonate with broad-spectrum activity against a wide variety of DNA viruses. It is reportedly effective in patients diagnosed with progressive multifocal leukoencephalopathy, an infection caused by JC virus. Cidofovir is usually administered in a dosage of 5 mg/kg, with approximately 75–80% of the cidofovir dose excreted in the urine unchanged within 24 hours of administration. In addition, cidofovir is usually given in conjunction with the anti-diuretic probenecid. Cidofovir is nephrotoxic and, therefore, is contraindicated in patients with impaired renal function. Nevertheless, cidofovir was studied herein for its effect on BKV load in kidney transplant recipients diagnosed with BKV associated nephropathy.

BRIEF SUMMARY OF THE INVENTION

Provided are PCR primers for the quantitation of BKV viral loads in a sample using a PCR or quantitative PCR (QPCR) assay and methods for the diagnosis and management of BKVN. PCR primers are provided for binding to and amplifying a region of the BKV genome using PCR or QPCR. The PCR primers include a forward BKVN primer, preferably including substantially the sequence 5'-TGATAGCCCAGAGAGAAAAATGC-3' (SEQ ID NO: 1), and/or a derivative thereof, and a reverse BKVN primer, preferably including substantially the sequence 5'-TCCACAGGTTAGGTCCTCATTTAAA-3' (SEQ ID NO: 2), or a derivative thereof.

Also provided is a method for quantitating the BKV viral load in a viruria, serum or plasma (viremia) tissue sample using one or more of the BKNV primers, or derivatives thereof, in a PCR or QPCR assay. The method includes the steps of: performing a nucleic acid purification method on a patient specimen to obtain a nucleic acid test sample; conducting PCR or QPCR on the test sample using an appropriate primer set, as defined herein, to generate an amplicon if BKV target sequences are present in the test sample; and detecting the presence of BKV specific amplicon in the sample. A multiplexed QPCR method also is provided using the above-described primer set in combination with a second PCR primer set.

A method also is provided for the management of BKVN in renal transplant recipients using cidofovir, preferably without co-administration of an anti-diuretic such as probenecid. The method includes quantitating the BKV viral load in a patient specimen and administering to a patient a dosage of cidofovir effective to reduce BKV viral load in the patient. Patients treated according to the method have shown clearance of BKV viruria after 2–4 doses of the drug.

Also provided is a kit containing a PCR primer, or a derivative thereof, for quantitating BKV viral load in a sample using a PCR assay, for use in diagnosing and managing BKVN. The kit may further comprise, without limitation control nucleic acids, primer sets to generate a second amplicon in a multiplexed PCR or QPCR assay; collection containers; a buffer; nucleic acid purification reagents or kits; a mixture of dNTP's; and a thermostable DNA polymerase.

Other details, objects and advantages of the present invention will become apparent with the following description.

BRIEF DESCRIPTION OF THE DRAWINGS

The following drawing is for illustrative purposes to facilitate better understanding of the invention and not for limiting the same.

FIG. 1 provides the complete nucleotide sequence of the Dunlop strain of BKV (SEQ ID NO: 3), GenBank Accession No. NC 001538.

DETAILED DESCRIPTION OF THE INVENTION

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within these ranges. Also, the disclosure of these ranges is intended as a continuous range including every value between the minimum and maximum values.

Described herein is a polymerase chain reaction (PCR) method that is useful in the diagnosis and management of BKVN. The PCR primers described herein are specific for BKV when performed on nucleic acids extracted from blood derivatives, including serum or plasma, urine or tissue samples using QPCR. Finally, the following description shows that cidofovir therapy is useful in the treatment of BKVN in renal transplant recipients.

PCR primers are provided for use in amplifying a region of the BKV genome using PCR assays. The PCR primers are oligonucleotides and include a forward BKVN primer substantially including the sequence 5'-TGATAGCCCAGAGAGAAAAATGC-3' (SEQ ID NO: 1), or a derivative thereof and a reverse BKVN primer substantially including the sequence 5'-TCCACAGGTTAGGTCCTCATTTAAA-3' (SEQ ID NO: 2), or a derivative thereof.

As used herein, the term "oligonucleotide" is intended to embrace not only DNA oligonucleotides, but functional analogs thereof. Functional analogs are oligomeric compounds that are suitable for use as primers in a PCR reaction and therefore have adequate sequence specificity and ability to be elongated by a selected thermophilic polymerase in a PCR reaction. There is no strict size limit to an "oligonucleotide" as defined herein, only that the oligonucleotide can be used in a PCR reaction. As such, there are maximum and minimum functional limits to the size of the oligonucleotide. The minimum size is often dictated by the need for adequate sequence specificity of the oligonucleotide and the maximum size is often dictated by the $T_m$ (melting temperature) of the oligonucleotide, along with other factors important in creating a robust PCR environment. As such, optimized oligonucleotide PCR primers may range from 10 to 35 bases in length, more typically from 15 to 25 bases in length and most typically are about 20 bases long.

The two primers provided above both bind to and amplify a portion (substantially including bases 1797 to 1881 of SEQ ID NO: 3) of the late region of the BKV genome, specifically the VP-1 region of the genome. The forward BKVN primer hybridizes to a target sequence that substantially includes base: 1979 to 1819 of SEQ ID NO: 3. The reverse BKVN primer hybridizes to a target sequence that is bases 1857 to 1881 of SEQ ID NO: 3. The forward BKVN primer may be used in conjunction with a reverse primer that binds downstream of the above reverse BKVN primer. Alternatively, the reverse primer may be used in conjunction with a forward primer that binds upstream of the above forward primer. The terms "upstream" and "downstream" refer to the relative positions along a DNA sequence in the traditional 5' to 3' direction such that an upstream region is 5' of a downstream region.

In addition, for any nucleic acid sample to be tested by the PCR assay, a second control PCR assay may be performed using a different (control) set of PCR primers than the BKVN primers (SEQ ID NOS: 1 and 2). The control primers will amplify segments of a broader set of BKV subtypes, with all BKV subtypes or with all polyoma viruses. One example of a primer set that amplifies BKV sequences from a broader range of BKV subtypes than does the BKVN primer set is a VP-1 control primer set including the following primers:

Forward 5'-GCAGCTCCCAAAAAGCC-3'   (SEQ ID NO: 5)

Reverse 5'TTCCACAGGTTAGGTCCTCA-3'  (SEQ ID NO: 6), or analogs or derivatives thereof. As shown below, this primer set identifies both BKVN-associated and non-BKVN-associated BKV subtypes in urine, while the BKVN primer set identifies viruria only in BKVN patients.

Other suitable control PCR assays utilize primer sets that are specific to a broader range of BKV subtypes or polyoma viruses than the BKVN primer set. An example of a primer set that would identify all polyoma viruses is a T antigen-specific primer set, such as those disclosed in Biel et al., (2000) "Rapid Quantification and Differentiation of Human Polyomavirus DNA in Undiluted Urine from Patients after Bone Marrow Transplantation," *J. Clin. Microbiology* 38(10): 3689–95 and Limaye et al., (2000) Quantitation of BK Virus Load in Serum for the Diagnosis of BK Virus-associated Nephropathy in Renal Transplant Recipients," *J. Infectious Diseases* 183:1669–72, both of which are incorporated herein by reference in their entirety. Additional suitable control primer sets amplify non-viral sequences, such as, without limitation, human GAPDH and human 18S ribosomal RNA, which are available commercially from Applied Biosystems.

As stated above, the primers may have one of the nucleic acid sequences above or may be a derivative of one of the above sequences. The term "derivative," as used herein, is any oligonucleotide that has similar binding characteristics to a target DNA sequence as one of the above two primers, SEQ ID NO: 1 or SEQ ID NO: 2, and, therefore, is useful as a PCR or QPCR primer as described herein. For example, and without limitation, a derivative may be formed by attaching, inserting or deleting one or more nucleic acids to or from one of the above primer sequences, for instance by the addition of a restriction site to the 5' end of one or both of the primers. As an additional non-limiting example, SEQ ID NOS: 2 and 6, or versions thereof with the addition or deletion of certain 5' or 3' flanking nucleotides, may be considered derivatives of each other. Also, a derivative may include one or more nucleotides that are derivatized to contain functional groups, or altered nucleotides, such as inosine. Generally, it is preferred that the derivative contains from about 10 to about 35 nucleic acids, but it may contain more or less nucleotides, depending on a number of empirical factors that impact the usefulness of any given primer in a PCR reaction. The only limitation to the analogs or derivatives is that they hybridize to the desired target sequence of the BKV genome (for instance, for the BKVN primer set, the sequences of SEQ ID NOS: 1 and 2) and can serve as a PCR or QPCR primer, as can be determined empirically by a person of skill in the art.

A PCR assay or method also is provided for rapidly and accurately detecting the presence of BKVN in tissues or bodily fluids and thereby providing a tool for the management of BKV patients. A PCR assay or method is a procedure whereby a segment of a nucleic acid molecule, is amplified repetitively and exponentially to produce a large amount of DNA molecules (amplicons) which consist only of the amplified segment. The procedure requires a large number of replication cycles, usually 20 to 40 cycles. In each cycle, two oligonucleotide primers bind to complementary strands of the nucleic acid molecule and define the limits of the amplified portion. A primer-dependent polymerase then replicates the strands to which the primers have bound. Thus, in each cycle, the number of DNA duplexes is doubled. This general procedure and numerous variations thereof are well known to those skilled in the art.

The first step of the PCR method involves obtaining a nucleic acid from a patient specimen. The patient specimen can be any tissue or bodily specimen. However, it is preferred that the specimen be one of a urine specimen, a serum specimen, or a kidney tissue specimen, obtained from a patient by standard methods. A urine specimen can be collected in a container. A plasma specimen may be obtained from whole blood collected in a heparin coated test tube and then spun in a centrifuge at a speed sufficient to separate the blood into two layers: a cellular layer and a plasma layer. The plasma layer is then collected. A kidney tissue specimen may be obtained by biopsy.

After obtaining a specimen, DNA in the specimen, if present, is purified to the extent necessary for detection of target nucleic acid by PCR and/or QPCR. Such purification methods are well known in the art and include a variety of techniques including extractions, precipitations and chromatographic methods. Kits for the purification of nucleic acids from tissue specimens, including bodily fluids, are commercially available from many sources, including Quiagen, Inc., of Valencia, Calif. Once purified, the DNA can be diluted in water or a buffer system suitable for conducting a PCR reaction. At any time, part of the specimen may be used for analysis while the remaining part of the sample may be stored. For example, part of the specimen can be stored in a freezer at −70° C.

When the sample is a tissue specimen, DNA must be extracted from the specimen. A variety of methods are known to be useful for liberating nucleic acid from cells and virus in the specimen. As above, kits for isolation of viral nucleic acid from tissue are commercially available, for instance from Quiagen, Inc.

In the DNA purification step, certain specimens may not contain sufficient amounts of nucleic acid to reproducibly purify DNA from the specimen. In such a case, it may be desirable to add a carrier to the specimen before purifying the DNA. A variety of carriers are known in the art, including, without limitation, DNA, RNA and glycogen or combinations thereof, but can be any compound or composition that can enhance the sensitivity and/or reproducibility of the DNA purification step. The choice of carrier, and how much carrier is added to a given specimen would depend on the choice of DNA purification assay and empirical factors that readily can be optimized by a person of skill in the art.

A carrier might contain a control DNA, preferably not containing a non-human or polyoma virus sequence that can be amplified by PCR. The control DNA would include a sequence that would provide an internal reference to account for variations in the efficiency of the DNA purification procedure. In a multiplex QPCR procedure, an additional primer set and TaqMan probe can be used that specifically amplifies and detects sequences found specifically in the control DNA. If a specific amount of control DNA is added to every specimen, the results of the BKNV-specific QPCR could be adjusted to account for variations in the DNA purification step. The control DNA might be a part of the carrier itself, for instance, and without limitation, if non-human genomic DNA is used as a carrier. However, in that case the control DNA might be too prevalent in a given sample. If that is the case, the carrier might include both a carrier portion, such as genomic DNA or glycogen, and an appropriately diluted control DNA, such as, without limitation, plasmid DNA including a sequence to be amplified.

The next step involves conducting PCR or QPCR on any purified isolated from the specimen (the test sample) using a BKNV primer, or a derivative thereof, to generate an amplicon. The theories and mechanisms of PCR and QPCR are well known in the art, along with variations in these techniques. Similarly, a large variety of suitable PCR and QPCR protocols are broadly available and are useful in the assays described herein with no modification or with modification that can be readily determined and optimized empirically. These primers are able to bind to and amplify a specific portion of the BKV genome, which is useful in the diagnosis and management of BKVN.

Suitable reaction mixtures or compositions for conducting PCR and/or QPCR on a nucleic acid sample contain at least a portion of a purified nucleic acid test sample prepared as described above; one or more primers, at least one of which is selected from SEQ ID NO: 1 and SEQ ID NO: 2, or analogs or derivatives thereof; a mixture of deoxynucleotide triphosphates (dNTP's); and a thermostable DNA polymerase in a buffered solution, typically containing magnesium. A thermostable DNA polymerase is a DNA polymerase, such as Taq, Pfu or Tfl polymerases, that is capable of elongation at elevated temperatures, typically greater than 40° C. Magnesium, in the form of magnesium ion, typically is an element of a PCR reaction.

Next, the PCR and/or QPCR reaction solution is cycled. Typical PCR reactions include three steps, a denaturation step, an annealing step and an elongation step. The annealing steps may be performed as part of the same step at the same temperature, as shown in the examples below.

The next step of one method described herein is to detect the production of a BKV-specific amplicon. In a non-quantitative assay, the BKV-specific amplicon may be detected in an ethidium bromide stained agarose gel according to standard methods. The amount of BKV nucleic acid in a test sample may be quantitated by comparing the amount of BKV-specific amplicon produced versus a control. The probe can be any nucleic acid that can bind to the BKV-specific amplicon. For instance, the probe may have the nucleic acid sequence 5'-TTACAGCACAGCAAGAATTCCCCTCCC-3' (SEQ ID NO: 4). The probe can be labeled so that binding of the probe to the amplicon may be detected. The label can be any sort of label known in the art, for instance, fluorescent, radioactive, enzyme or antigenic labels. In one example, the 5' end of the probe may be labeled with a FAM dye and/or the 3' end of the probe be labeled with a TAMRA dye.

A QPCR method involves quantitating the amount of BKV nucleic acid in the nucleic acid sample. This is done by comparing the production rate of the BKV-specific amplicon product versus the production rate of a control DNA sequence or amplicon. A control DNA sequence or amplicon is a non-target nucleic acid sequence of known quantity that is used to calculate the amount of target BKV nucleic acid in the sample. The products of the QPCR process may be compared to control samples after a fixed number of PCR cycles to determine the relative virus load in the tissue or bodily fluid. One method of comparing the relative quantities of the products of the QPCR process is by gel electrophoresis, for instance, by running the samples on a gel and detecting those samples by one of a number of known methods including, without limitation, Southern blotting and subsequent detection with a labeled probe, staining with ethidium bromide and incorporating fluorescent or radioactive tags in the amplicons.

However, the progress of the PCR reaction typically is monitored by analyzing the relative rates of amplicon production for each PCR primer set in real time. Monitoring amplicon production may be achieved by a number of processes, including without limitation, fluorescent primers, fluorogenic probes and fluorescent dyes that bind double-stranded DNA. A common method is the fluorescent 5' nuclease assay. This method exploits the 5' nuclease activity of certain thermostable DNA polymerases (such as Taq or Tfl DNA polymerases) to cleave an oligomeric probe during the PCR process. The oligomer is selected to anneal to amplified sequences under elongation conditions. The probe typically has a fluorescent reporter on its 5' end and a fluorescent quencher of the reporter at the 3' end. A probe useful in this process is preferably the probe having the nucleic acid sequence 5'-TTACAGCACAGCAAGAATTCCCCTCCC-3' (SEQ ID NO: 4). In addition, the probe can be labeled so that binding of the probe to the amplicon may be detected. The label can be any sort of label known in the art. In one embodiment, the 5' end of the probe is labeled with a FAM dye and the 3' end of the probe is labeled with a TAMRA dye. So long as the oligomer is intact, the fluorescent signal from the reporter is quenched. However, when the oligomer is digested during the elongation process, the fluorescent reporter is no longer in proximity to the quencher. The relative accumulation of free fluorescent reporter for a given amplicon may be compared to the accumulation of the same amplicons for a control sample and/or to that of a control gene, such as β-actin or 18S rRNA to determine the relative abundance of a given cDNA product of a given RNA in a RNA population. Products and reagents for the fluorescent 5' nuclease assay are readily available commercially, for instance from Applied Biosystems of Foster City, Calif.

Equipment and software also are readily available for monitoring amplicon accumulation in PCR and QPCR according to the fluorescent 5' nuclease assay and other QPCR procedures, including the ABI Prism 7700 Sequence Detection System (TaqMan), commercially available from Applied Biosystems.

The procedures described herein also may be used in multiplex QPCR processes. In its broadest sense, a multiplex PCR process involves production of two or more amplicons in the same reaction vessel. Multiplex amplicons may be analyzed by gel electrophoresis and detection of the amplicons by one of a variety of methods, such as, without limitation ethidium bromide staining, Southern blotting and hybridization to probes, or by incorporating fluorescent or radioactive moieties into the amplicons and subsequently viewing the product on a gel. However, real-time monitoring of the production of two or more amplicons is preferred. The fluorescent 5' nuclease assay is the most common monitoring method. Equipment is now available (for example, the above-described Amplified Biosystems product) that permits the real-time monitoring of accumulation of two or more fluorescent reporters in the same tube. For multiplex monitoring of the fluorescent 5' nuclease assay, oligomers are provided corresponding to each amplicon species to be detected. The oligomer probe for each amplicon species has a fluorescent reporter with a different peak emission wavelength than the oligomer probe(s) for each other amplicon species. The accumulation of each unquenched fluorescent reporter can be monitored to determine the relative amounts of the target sequence corresponding to each amplicon.

In traditional multiplex QPCR procedures, the selection of PCR primer sets having similar annealing and elongation kinetics and similar sized amplicons are desirable. The design and selection of appropriate PCR primer sets is a process that is well known to a person skilled in the art. The process for identifying optimal PCR primer sets, and respective ratios thereof to achieve a balanced multiplex reaction also is known. By "balanced," it is meant that certain amplicon(s) do not out-compete the other amplicon(s) for resources, such as dNTPs. For instance, by limiting the abundance of the PCR primers for the more abundant RNA species in an RT-PCR (reverse transcriptase polymerase chain reaction) experiment will allow the detection of less abundant species. Equalization of the Tm (melting temperature) for all PCR primer sets also is encouraged. See, for instance, ABI PRISM 7700 Sequence Detection System User Bulletin #5, "Multiplex PCR with TaqMan VIC Probes," *Applied Biosystems* (1998/2001), incorporated herein by reference. For example, a second primer set that could be used is a set of primers including SEQ ID NOS: 5 and 6 or a primer set that produces a polyoma T antigen-specific amplicon, as described above.

In the commercialization of the above-described methods for PCR, QPCR and multiplexed QPCR, certain kits for detection of BKV nucleic acids will be particularly useful. One example of such a kit would include reagents necessary for the one-tube multiplexed QPCR process described above. In one example, the kit would include the above-described reagents, including a corresponding PCR primer set, a thermostable DNA polymerase, such as Taq polymerase, and a suitable fluorescent reporter, such as, without limitation, a probe for a fluorescent 5' nuclease assay, a molecular beacon probe, a single dye primer or a fluorescent dye specific to double-stranded DNA, such as ethidium bromide. Thermostable DNA polymerases are commonly and commercially available from a variety of manufacturers. Additional materials in the kit may include: suitable reaction tubes or vials; a barrier composition, typically a wax bead, optionally including magnesium; reaction mixtures (typically 10x) for the PCR reaction, including, without limitation, necessary buffers and reagents, such as dNTP's; nuclease free water; control nucleic acid(s) and/or any additional buffers, compounds, co-factors, ionic constituents, proteins and enzymes, polymers, and the like that may be used in PCR or QPCR reactions.

The constituents of the kits may be packaged together or separately, and each constituent may be presented in, without limitation, one or more tubes or vials, or in cartridge form (a modular unit containing one or more reagents for use in an automated device), as is appropriate. Such tubes, vials or cartridges are referred to herein generically as "containers." The constituents, independently or together, may be packaged in a variety of states, including without limitation, in lyophilized, glassified, aqueous or other forms as is appropriate.

Also provided herein is a method for the management of BKVN in renal transplant recipients using cidofovir. The method includes quantitating the BKV viral load in a patient specimen and administering to a patient a dosage of cidofovir effective to reduce BKV viral loads in the patient. The first step of quantitating the BKV viral load in the patient specimen can be accomplished through the use of the above-described primers and methods for quantitating the BKV viral load in a specimen.

The second step is administering to the patient a dosage of cidofovir effective to reduce BKV viral loads in the patient. Cidofovir typically is administered in a dosage of at least about 5 mg/kg. In addition, cidofovir is usually administered in conjunction with an anti-diuretic, probenecid. However, in the present method, cidofovir is administered in a specific low dosage, typically without probenecid. A dosage effective to reduce BKV viral loads in a patient, as used in this application, means a dosage of from about 0.25 mg/kg to about 1.0 mg/kg, 2–3 times weekly. The dosage level typically is based upon a number of factors including, without limitation, the patient's BKV viral load, the responsiveness of the BKV viral load to previous doses of cidofovir and external indicators of kidney function, such as creatinine levels.

Treatment with cidofovir can improve a patient's graft prognosis because the dosage can be adjusted to ensure that the viral infection is controlled, without reducing immunosuppression and possibly causing rejection of the graft.

EXAMPLES

Study Population

All kidney transplant patients in the study underwent a routine protocol transplant biopsy at 1 week, 1 month, and 1 year following renal transplantation. Additional biopsies were performed based upon clinical considerations, such as an unexplained rise in serum creatinine that exceeded 20% above the baseline value.

127 patients undergoing renal allograft biopsies were studied. Each patient had samples of blood and urine collected the same day that the renal allograft biopsy was performed. Subsequent collection of urine and blood samples were collected if the clinical situation of the patient changed or if any therapeutic changes in the immunosuppressive regimen were made.

An additional 28 biopsy proven BKVN patients were also studied. Blood and urine samples were also taken from this group at various intervals, as directed by clinical presentation. Two to 15 each of blood and urine samples were taken from each patient.

Sample Collection

50–100 cc of fresh urine from each patient was collected in a sterile container. Of the amount collected, 5 cc of urine was stored at −50° C. The remainder of the urine specimen was processed according to the below procedure.

5–7 cc of blood from each patient was collected in an EDTA tube. The blood was then centrifuged and the plasma collected. Of the amount collected, 1 cc of the plasma was stored at −50° C. The remainder of the plasma sample was processed according to the below procedure.

Sample Processing

Nucleic acid was extracted from urine and plasma specimens (150 μl of urine or plasma per specimen) using the Qui Amp Viral RNA Minikit, commercially available from Qiagen, Inc. The extraction procedure was performed according to the manufacturer's instructions provided with the kit.

The nucleic acid content in each sample was determined by Picogreen dye (LS-50™, Perkin Elmer).

Quantitation of BKV Viral DNA Using TaqMan Real Time PCR

A BKV gene sequence from the VP-1 region was amplified by the real-time TaqMan QPCR assay using the following primers and probe. The forward BKVN primer had the sequence 5'-TGATAGCCCAGAGAGAAAAATGC-3' (SEQ ID NO. 1) and a $T_m$ of 59° C. The reverse BKVN primer had the sequence 5'-CCACAGGTTAGGTCCTCATTTAAA-3' (SEQ ID NO. 2) and a $T_m$ of 59° C. The TaqMan probe had the sequence 5'-TTACAGCACAGCAAGAATTCCCCTCCC-3' (SEQ ID NO. 4) and a $T_m$ of 68° C. The TaqMan probe was labeled at the 5' end with a FAM dye and at the 3' end with a TAMRA dye. The primers and probe were synthesized by Operon Technologies.

The primers were found to be specific for BKV by testing against JC and BKV stocks obtained from The American Type Culture Collection.

The reaction mixture included:

12.5 µl TaqMan (2x) universal Master Mix (Part No. 4304437, Applied Biosystems)

1 µl 10 millimolar (mm) Forward primer

1 µl 10 mm Reverse primer

1 µl 5 nanomolar BKV probe qs water to 25 µl.

The reaction mixture was cycled as follows:

50° C. for 2 minutes;

95° C. for 10 minutes; and 40 cycles of two-step PCR including for each cycle:

95° C. for 15 seconds; and

60° C. for one minute.

Progression of the reaction monitored by an ABI Prism 7700 Sequence Detection System.

In order to generate a positive control, a BKV gene sequence from the VP-1 region encompassing the TaqMan primer amplicon was cloned in a vector using the pGEM-T PCR cloning system (Promega, Madison, Wis.). The above sequence was then quantitated using UV spectrophotometry in order to calculate the copy number for a master standard positive control. A 10x serial dilution of standard positive control, with copies ranging from $10^7$ to $10^{10}$ was made and used to generate a standard curve with each quantitative assay. The samples were run in duplicate. The urinary viral load was expressed as BKV copies/µl of urine. The plasma viral load was expressed as BKV copies/µl.

Variation and Detection

The intra-assay coefficient of variation was 19%. The inter-assay coefficient of variation was 30%. The lower limit of detection was determined to be 10 viral copies.

EXAMPLE 1

Renal Transplant Recipients

The urinary and plasma viral loads for the BKVN group were as follows. Urinary PCR values ranged from about $10^3$ to greater than about $10^7$ copies/µl urine. Plasma PCR values were positive for 4–6 weeks following transplantation in four of 14 patients tested, but became negative after the immunosuppression was reduced. BKV viruria was detectable in all the biopsy-proven BKVN patients when tested within two weeks of biopsy diagnosis. Some patients continued to exhibit viruria even after 12–18 months after diagnosis if not treated with cidofovir.

EXAMPLE 2

Non-BKVN Patients

In addition to the biopsy-proven patients, significant viruria was detected by QPCR in four patients who were diagnosed as having acute rejection but did not have viral inclusion bodies on immunostaining of the transplant biopsy. Two of these patients subsequently developed intranuclear characteristic inclusions of BKVN.

In contrast to urinary PCR (viruria), plasma PCR (viremia) was positive in only a small fraction of the patients and only for a relatively short duration. Plasma PCR appears to be helpful in identifying patients likely to have a more severe infection (viremia, as opposed to viruria), and a less favorable outcome.

EXAMPLE 3

Cidofovir Treatment

Four patients were treated with cidofovir at a dosage level of 0.25 to 1.0 mg/kg, 2–3 times weekly. This is 10–20% of the recommended dose of 5 mg/kg. In addition, cidofovir was administered without probenecid. All four patients showed clearance of BKV viruria after 2–4 doses of cidofovir. A summary of the clinical characteristics of the four patients is presented in Table 1, below.

TABLE 1

| | Patient No. - Diagnosis | | | |
| --- | --- | --- | --- | --- |
| | 1 - Post Urethral valve | 2 - Diabetic Nephropathy | 3 - Renal Dysplasia | 4 - IgA Nephropathy |
| Gender | M | F | M | M |
| Age at Transplantation | 10 | 54 | 4 | 29 |
| Time Between Transplantation and Diagnosis in Months | 12 | 9 | 22 | 11 |
| Number of Biopsies Prior to Transplantation | 3 | 3 | N/A | N/A |
| Creatinine Level at Diagnosis | 1.6 | 2.9 | 1.5 | 2.2 |
| Prograf Level at Diagnosis | 14.6 | 4.6 | 10.2 | 8 |
| Peak Creatinine | 3.3 | 8.1 | 7.2 | 6.4 |
| Current Creatinine | 1.8 | 3.2 | 1.7 | 3 |
| Number of Doses of Cidofovir and (mg/dose) | 3 (20-20-40) | 3 (70-35-15) | 1 (20) | 4 (200-200-200-70) |

EXAMPLE 4

Case Report (Patient #1)

Patient #1, at the time of the study, was a six year-old boy. He was diagnosed with end-stage renal disease secondary to renal dysplasia and bilateral vesicoureteral reflux and received a cadaveric kidney.

Immunosuppression consisted of tacrolimus (Prograf) and prednisone. Prednisone was tapered over the first six months after the transplant and then discontinued.

The post-transplant course was relatively uncomplicated, without any episodes of rejection. However, during a routine clinic visit, the patient had an elevated blood pressure (121/107 mm Hg) and an elevated serum creatinine (1.5 mg/dl, baseline was 0.9–1.0 mg/dl) and mild acidosis ($TCO_2$ 18 meq/L). The patient had complained of nasal congestion for three weeks and had an episode of gastroenteritis one month prior to the visit.

Upon admission to the clinic, the patient had a tacrolimus serum level of 7.3 ng/ml, a hematocrit of 28.9% with 9.0% white blood cells, 35% neutrophils, 51% lymphocytes, 6% monocytes and 8% eosinophils. CMV IgG and IgM were 6 and 0.2 units respectively. EBV-PCR was less than eight copies. An ultrasound of the transplanted kidney showed an indistinctly demarcated region of increased echogenicity in the mid portion of the allograft. This region appeared hypoperfused upon Doppler examination. Two allograft biopsy specimens were taken, one from the echogenic mass seen on ultrasound, and one from a normal appearing area of the kidney. The histologic appearances of both specimens were similar under microscopic examination, showing interstitial fibrosis, tubular atrophy, and focal areas of intense lymphocytic chronic inflammatory infiltrate, with mild tubilitis. In addition, there were many enlarged tubular epithelial cells, with inclusion filling most of the nucleus which stained positive for polyoma antigen. The patient's FK506 dosage was reduced to achieve levels around 5 ng/ml. A week later, the patient's creatinine showed an increase from 1.5 mg/dl to 1.9 mg/dl and he was readmitted.

Subsequently, the serum creatinine progressively rose to 8 mg/dl. At this point, a combination of IV IgG, high dose steroids and a single dose of cidofovir (1 mg/kg IV without probenecid) was administered. The urinary PCR showed a viral load of $10^5$ copies/ng of DNA as determined by the QPCR methods described herein.

Two months later, both urine and blood samples were taken. Neither sample was amplifiable for BKV. The patient subsequently resumed full immunosuppression and has continued to be viruria and viremia-free, with a serum creatinine of 1.7–1.9 mg/dl.

EXAMPLE 5
QPCR for Differentiating Nephropathic BKV from Non-Nephropathic BKV
VP-1 control Primers:

| | |
|---|---|
| Forward 5'GCAGCTCCCAAAAAGCC-3' | (SEQ ID NO: 5) |
| Reverse 5'TTCCACAGGTTAGGTCCTCA-3' | (SEQ ID NO: 6) |

Reaction conditions: reaction mixture and reaction conditions as described above.

Urine nucleic acid samples from patients, described above, were analyzed as above by QPCR using the VP-1 control primers. The same samples were analyzed earlier as described in Example 1 using the BKVN primer set. Of the 155 patients, 31 were positive for BKV using the VP-1 control primer set while only 28 were positive for BKV using the BKVN primer set corresponding to SEQ ID NOS: 1 and 2. Surprisingly, the three patients that showed positive viruria using the VP-1 control primers, but negative using the BKVN primer set showed no BKVN, while those patients showing viruria using both primer sets demonstrated active BKVN by biopsy.

In summary, QPCR can be a useful tool in the diagnosis and management of BKVN. Also, treatment with the drug cidofovir may improve a patient's graft prognosis. In addition, QPCR can help monitor a patient's response to cidofovir so that the dosage of this potentially nephrotoxic drug can be adjusted to ensure that exposure to the drug is no longer than needed for the control of polyomavirus infection.

The above invention has been described with reference to the preferred embodiment. Obvious modifications and alterations will occur to others upon reading and understanding the preceding detailed description and the claims. It is intended that the invention be construed as including all such modifications and alterations.

I claim:

1. A method of managing BKV-associated nephropathy in a renal transplant patient comprising administering to the renal transplant patient a dose of cidofovir effective to reduce BKV viral load in the patient.

2. The method of claim 1, wherein no anti-diuretic is administered to the patient at the same time as the cidofovir.

3. The method of claim 1, wherein a dose of up to about 1.0 mg/kg patient weight of cidofovir is administered to the patient up to about three times weekly.

4. The method of claim 3, wherein a dose of from about 0.25 mg/kg patient weight to about 1.0 mg/kg patient weight of cidofovir is administered to the patient two to three times weekly.

5. The method of claim 1, wherein one to four total doses of cidofovir are administered to the patient.

6. A method of managing BKV-associated nephropathy in a renal transplant patient comprising the steps of:
   (a) quantitating the BKV viral load in a specimen of the patient; and
   b) administering to the patient a dose of cidofovir effective to reduce BKV viral load in the patient, wherein the amount of cidofovir administered to the patient is based upon at least one of the BKV viral load in the specimen, the response of the BKV viral load in the patient to previous administrations of cidofovir and patient creatinine levels.

7. The method of claim 6, wherein the specimen is urine.

8. The method of claim 6, wherein the BKV viral load is determined by quantitative PCR.

9. A method of treating BKV-associated nephropathy in a renal transplant patient comprising administering to the renal transplant patient a dose of cidofovir effective to reduce BKV viral load in the patient.

10. The method of claim 9 wherein no anti-diuretic is administered to the patient at the same time as the cidofovir.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: VP-1 forward primer

<400> SEQUENCE: 1
tgatagccca gagagaaaaa tgc                                              23

<210> SEQ ID NO 2
<211> LENGTH: 25
<212> TYPE: DNA
<213> ORGANISM: Artificial Sequence
<220> FEATURE:
<223> OTHER INFORMATION: VP-1 reverse primer

<400> SEQUENCE: 2
tccacaggtt aggtcctcat ttaaa                                            25

<210> SEQ ID NO 3
<211> LENGTH: 5153
<212> TYPE: DNA
<213> ORGANISM: BK virus

<400> SEQUENCE: 3
```

-continued

```
ttttgcaaaa attgcaaaag aatagggatt tccccaaata gttttgctag gcctcagaaa        60
aagcctccac acccttacta cttgagagaa agggtggagg cagaggcggc ctcggcctct       120
tatatattat aaaaaaaaag gccacaggga ggagctgctt acccatggaa tgcagccaaa       180
ccatgacctc aggaaggaaa gtgcatgact cacaggggaa tgcagccaaa ccatgacctc       240
aggaaggaaa gtgcatgact cacagggagg agctgcttac ccatggaatg cagccaaacc       300
atgacctcag gaaggaaagt gcatgacaga catgttttgc gagcctagga atcttggcct       360
tgtccccagt taaactggac aaaggccatg ttctgcgcc agctgtcacg acaagcttca        420
gtgaaagttg gtaaaacctg gactggaaca aaaaaagag ctcagaggat ttttattttt        480
attttagagc ttttgctgga attttgtaga ggtgaagaca gtgtagacgg gaaaaacaaa       540
agtaccactg ctttacctgc tgtaaaagac tctgtaaaag actcctaggt aagtaatccc       600
ttttttttg tatttccagg ttcatgggtg ctgctctagc acttttgggg gacctagttg        660
ccagtgtatc tgaggctgct gctgccacag gattttcagt ggctgaaatt gctgctgggg       720
aggctgctgc tgctatagaa gttcaaattg catcccttgc tactgtagag ggcataacaa       780
gtacctcaga ggctatagct gctataggcc taactcctca acatatgct gtaattgctg        840
gtgctcctgg ggctattgct gggtttgctg ctttaattca aactgttagt ggtattagtt       900
ccttagctca agtagggtat aagttctttg atgattggga tcacaaagtt tccactgtag       960
gcctctatca gcaatcaggc atggctttgg aattgtttaa cccagatgag tactatgata      1020
ttctgtttcc tggtgtaaat acttttgtta ataatattca ataccttgat cctaggcatt      1080
ggggtccttc tttgtttgct actatttccc aggctttgtg gcatgttatt agggatgata      1140
taccttctat aacctcacag gaattgcaga gaagaacaga aagatttttt agagactcct      1200
tggctagatt tttggaggaa actacctgga caattgtaaa tgccctata aacttttata       1260
attatattca acaatattat tctgatcttt ccctattag gccctcaatg gttagacaag       1320
tagctgaaag ggaaggtacc cgtgtacatt ttggccatac ttatagtata gatgatgctg      1380
acagtataga agaagttaca caaagaatgg acttaagaaa tcaacaaagt gtacattcag      1440
gagagtttat agaaaaaact attgccccag gaggtgctaa tcaaagaact gctcctcaat      1500
ggatgttgcc tttacttcta ggcctgtacg ggactgtaac acctgctctt gaagcatatg      1560
aagatggccc caaccaaaag aaaaggagag tgtccagggg cagctcccaa aaagccaaag      1620
gaacccgtgc aagtgccaaa actactaata aaggaggag tagaagttct agaagttaaa       1680
actggggtag atgctattac agaggtagaa tgcttcctaa acccagaaat ggggatcca       1740
gatgaaaacc ttaggggctt tagtctaaag ctaagtgctg aaaatgactt tagcagtgat      1800
agcccagaga gaaaaatgct tccctgttac agcacagcaa gaattcccct ccccaattta      1860
aatgaggacc taacctgtgg aaatctactg atgtgggagg ctgtaactgt acaaacagag      1920
gttattggaa taactagcat gcttaacctt catgcagggt cacaaaaagt gcatgagcat      1980
ggtggaggaa aacctattca aggcagtaat ttccacttct ttgctgtagg tggagaaccc      2040
ttggaaatgc agggagtgct aatgaattac aggtcaaagt accctgatgg tactataacc      2100
cctaaaaacc caacagccca gtcccaggta atgaatactg accataaggc ctatttggac      2160
aaaaacaatg cttatccagt tgagtgctgg gtacctgatc ccagtagaaa tgaaaatgct      2220
aggtattttg ggactttcac aggaggggaa aatgttcccc cagtacttca tgtgaccaac      2280
acagctacca cagtgttgct agatgaacag ggtgtggggc ctctttgtaa agctgatagc      2340
```

-continued

```
ctgtatgttt cagctgctga tatttgtggc ctgtttacta acagtctctgg aacacaacag    2400 tggagaggcc ttgcaagata ttttaagatc cgcctgagaa aaagatctgt aaagaatcct    2460
tacccaattt cctttttgct aagtgacctt ataaacagga gaacccagag agtggatggg    2520
cagcctatgt atggtatgga atcccaggta gaagaggtta gggtgtttga tggcacagaa    2580
agacttccag gggacccaga tatgataaga tatattgaca acagggaca attgcaaacc    2640 aaaatgcttt aaacaggtgc ttttattgta catatacatt taataaatgc tgcttttgta    2700
taagccactt ttaagcttgt gttatttttgg gggtggtgtt ttaggccttt taaaacactg    2760
aaagccttta cacaaatgca actcttgact atgggggtct gacctttggg aatcttcagc    2820
aggggctgaa gtatctgaga cttgggaaga gcattgtgat tgggattcag tgcttgatcc    2880
atgtccagag tcttcagttt ctgaatcctc ttctcttgta atatcaagaa tacatttccc    2940
catgcatata ttatatttca tccttgaaaa agtatacata cttatctcag aatccagcct    3000
ttccttccat tcaacaattc tagattgtat atcagttgca aaatcagcta caggcctaaa    3060
ccaaattagc agtagcaaca aggtcattcc actttgtaaa attctttttt caagtaagaa    3120
ctctgagttt tgtaaggatt ttcttaaata tattttgggc ctaaaatcta tttgtcttac    3180
aaatctagct tgcagggttt tagggacagg atactcattc attgtaacca agcctggtgg    3240
aaatatttgg gttctttttgt ttaaatgttt cttttctaaa tttaccttaa cacttccatc    3300
taaataatct ctcaaactgt ctaaattgtt tattccatgt cctgaaggca aatcctttga    3360
ttcagctcct gtccctttta catcttcaaa aacaaccatg tactgatcta tagctacacc    3420
tagctcaaag gttagccttt ccatgggtag gtttacattt aaggctttac caccacacaa    3480
atctaataac cctgcagcta gtgttgtttt tccactatca atgggacctt taaataacca    3540
gtatcttctt ttaggtacat tgaaaacaat acagtgcaaa aaatcaaata ttacagaatc    3600
cattttaggt agcaaacagt gcagccaagc aacacctgcc atatattgtt ctagtacagc    3660
atttccatga gctccaaata ttaaatccat tttatctaat atatgattga atctttctgt    3720
tagcatttct tccctggtca tatgaagggt atctactctt tttttagcta aaactgtatc    3780
tactgcttgc tgacaaatac ttttttgatt tttactttct gcaaaaataa tagcatttgc    3840
aaagtgcttt tcatgatact taagtgata aggctggtct tttttctgac actttttaca    3900
ctcctctaca ttgtattgaa attctaaata catacctaat aataaaaaca catcctcaca    3960
ctttgtctct actgcatact cagtaattaa tttccaagac acctgctttg tttcttcagg    4020
ctcttctggg ctaaaatcat gctcctttaa gccccccttga atgctttctt ctatagtatg    4080
gtatggatct ctagttaagg cactatatag taagtattcc ttattaacac ccttacaaat    4140
taaaaaacta aaggtacaca gcttttgaca gaaattatta attgcagaaa ctctatgtct    4200
atgtggagtt aaaaagaata taatattatg cccagcacac atgtgtctac taataaaagt    4260
tacagaatat ttttccataa gttttttata cagaatttga gcttttttctt tagtagtata    4320 cacagcaaag caggcaaggg ttctattact aaatacagct tgactaagaa actggtgtag    4380
atcagaggga aagtctttag ggtcttctac ctttcttttt ttttggggtg gtgttgagtg    4440
ttgagaatct gctgttgctt cttcatcact ggcaaacata tcttcatggc aaaataaatc    4500
ttcatcccat tttcatttaa aggaactcca ccaggactcc cactcttctg ttccataggt    4560
tggcacctat aaaaaaaata attacttagg gccttttaat atttttattat ttatctaaat    4620 ataagttagt taccttaaag ctttagatct ctgaaggggag tttctccaat tatttggacc    4680
caccattgca gagtttcttc agttaggtct aagccaaacc actgtgtgaa gcagtcaatg    4740
```

-continued

```
cagtagcaat ctatccaaac caagggctct tttcttaaaa attttctatt taaatgcctt    4800
aatctaagct gacatagcat gcaagggcag tgcacagaag gcttttgga acaaataggc     4860 cattccttgc agtacagggt atctgggcaa agaggaaaat cagcacaaac ctctgagcta   4920
ctccaggttc caaaatcagg ctgatgagct acctttacat cctgctccat tttttttatac  4980 aaagtattca ttctcttcat tttatcctcg tcgccccctt tgtcagggtg aaattcctta   5040
cacttcctta aataagcttt tctcattaag ggaagatttc cccaggcagc tctttcaagg   5100
cctaaaaggt ccatgagctc catggattct tccctgttaa gaactttatc cat          5153
```

```
<210> SEQ ID NO 4
<211> LENGTH: 27
<212> TYPE: DNA
<213> ORGANISM: Artificial Sequence
<220> FEATURE:
<223> OTHER INFORMATION: VP-1 probe

<400> SEQUENCE: 4
ttacagcaca gcaagaattc ccctccc                                         27

<210> SEQ ID NO 5
<211> LENGTH: 17
<212> TYPE: DNA
<213> ORGANISM: Artificial Sequence
<220> FEATURE:
<223> OTHER INFORMATION: VP-1 control forward primer

<400> SEQUENCE: 5
gcagctccca aaaagcc                                                    17

<210> SEQ ID NO 6
<211> LENGTH: 20
<212> TYPE: DNA
<213> ORGANISM: Artificial Sequence
<220> FEATURE:
<223> OTHER INFORMATION: VP-1 control reverse primer

<400> SEQUENCE: 6
ttccacaggt taggtcctca                                                 20
```